United States Patent [19]

Gaetzi et al.

[11] 3,971,647

[45] July 27, 1976

[54] COMPOSITION FOR THE REGULATION OF PLANT GROWTH

[75] Inventors: Karl Gaetzi, Basel; Hanspeter Fischer, Bottmingen, both of Switzerland

[73] Assignee: Ciba-Geigy Corporation, Ardsley, N.Y.

[22] Filed: Aug. 28, 1974

[21] Appl. No.: 501,395

Related U.S. Application Data

[63] Continuation-in-part of Ser. No. 340,428, March 12, 1973, abandoned.

[30] Foreign Application Priority Data

Mar. 17, 1972 Switzerland.................... 4058/72

[52] U.S. Cl..................................... 71/76; 71/70; 71/86; 71/103; 71/121; 260/564 R
[51] Int. Cl.²........................................... A01N 5/00
[58] Field of Search............................ 71/76, 121

[56] References Cited

UNITED STATES PATENTS

| | | | |
|---|---|---|---|
| 2,668,758 | 2/1954 | Roos et al.................... | 71/70 |
| 2,845,458 | 7/1958 | Lecher et al................. | 260/564 R |
| 3,084,192 | 4/1963 | Smathers..................... | 71/121 |
| 3,156,554 | 11/1964 | Tolbert........................ | 71/76 |
| 3,189,648 | 6/1965 | Gerjovich.................... | 71/121 X |
| 3,305,550 | 2/1967 | Koenig et al................. | 260/564 R |
| 3,385,891 | 5/1968 | Fenton......................... | 260/564 R |
| 3,511,879 | 5/1970 | Fuks et al.................... | 260/564 R |
| 3,598,800 | 8/1971 | Gatzi........................... | 260/293 |
| 3,657,346 | 4/1972 | Duerr........................... | 260/564 R |
| 3,884,670 | 5/1975 | Zeeh et al.................... | 71/76 |

OTHER PUBLICATIONS

Krewson et al., "Synthesis and Biol. Activity etc.," (1959), J. Agr. & Food Chem. 7, pp. 264–268, (1959).

*Primary Examiner*—Glennon H. Hollrah
*Attorney, Agent, or Firm*—Harry Falber

[57] ABSTRACT

The present invention relates to compositions and methods for the regulation of plant growth, especially for the inhibition of the growth of dicotyledonous plants by the use as active substance of quaternary ammonium salts of formula I

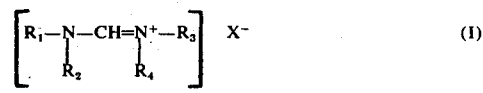

wherein $R_1$ and $R_2$ each independently represent an alkyl radical having 2 to 6 carbon atoms, an alkenyl radical having 3 to 5 carbon atoms, $R_3$ represents an alkyl radical of 8 to 14 carbon atoms $R_4$ represents an alkyl radical of 1 to 2 carbon atoms and $X^-$ is the conjugated ion of a strong acid.

These quaternary ammonium salts are new compounds.

4 Claims, No Drawings

COMPOSITION FOR THE REGULATION OF PLANT GROWTH

CROSS-REFERENCE TO RELATED APPLICATION:

This is a Continuation-in-part of our application Ser. No. 340,428, filed Mar. 12, 1973, now abandoned.

DETAILED DISCLOSURE:

The present invention relates to new quaternary ammonium salts of formamidine, their production, their use for the regulation of plant growth and compositions containing these quaternary ammonium salts.

The quaternary ammonium salts correspond to formula I

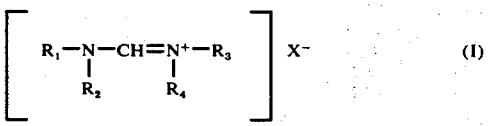

The symbols in this formula have the following meanings:

$R_1$ and $R_2$ each independently represent an alkyl radical having 3 to 5 carbon atoms, an alkenyl radical having 3 to 5 carbon atoms, $R_3$ represents an alkyl radical having 8-14 carbon atoms, $R_4$ represents an alkyl radical having 1-12 carbon atoms and $X^-$ is the conjugated ion of a strong acid.

Alkyl radicals denoted by $R_1$, $R_2$, $R_3$ and $R_4$ in this formula are straight-chain or branched radicals. The symbols $R_1$, $R_2$ and $R_4$ represent, for example, ethyl, n-propyl, isopropyl, n-butyl, isobutyl,sec-butyl, tert-butyl, as well as n-pentyl, $R_4$ also methyl, n-hexyl, n-octyl, n-octyl, n-decyl or n-dodecyl radicals and isomers. Straight-chain alkyl radicals having 8 to 14 carbon atoms are preferred as $R_3$. The symbols $R_1$ and $R_2$ can also represent alkenyl radicals having 3-5 carbon atoms, such as allyl, methallyl. butenyl and pentenyl radicals; the allyl radical is preferred.

Suitable quaternary ammonium salts are preferably salts of strong acids such as hydrohalic acids, phosphoric acid, sulphuric acid, methanesulphonic acid or toluene-sulphonic acid.

The quaternary ammonium salts of the formamidine of formula I are new compounds. They are produced in a manner known per se by alkylation of formamidines, which will be mentioned in detail further on in the text.

The position of the alkyl group $R_4$ thus introduced is either on the $N^1$ or the $N^2$ nitrogen atom of the formamidine molecule.

The quaternary ammonium salts of formula I are well suited for growth-regulation e.g. growth inhibition, abscission, defoliation and desication of unlignified parts of preferably dicotyledonous plants above the soil. These active substances or the compositions containing them are valuable for the removal of the foliage of a wide variety of cultivated plants. The plant itself and likewise the fruit or other crops are not damaged; the after-ripening necessary in many cases thus occurs without impairment. The active substances produce no morphological changes which would results in the withering of the plant. The action differs therefore from that of a herbicidal active substance. The compositions according to the invention can also be used for the treatment of plant material intended for seed production and for transportation.

The extent of the action is dependent on a variety of factors; it is dependent particularly on the time of application with regard to the stage of development of the plants, and on the applied concentration. Cultivated crops, such as cotton, leguminosae, sorghum, soya bean, potatoes, grape vines, etc., are treated before harvesting.

Of particular interest is the use of the quaternary ammonium salts of formula I for inhibiting or retarding the growth of dicotyledonous plants, among them especially soya and wood plants like trees and bushes.

The retardation of the vegetative growth of soybeans is of great practical importance.

The soybean is well known for its inefficiency from at least two aspects: Only about 50% of its leaves intercept light for photosynthesis with the others becoming parasites. And, only about 20% of the total sugar photosynthesized is converted into beans. The remaining 80% of photosynthate is used for the production of vegetative tissue, nutrition of the nitrogenfixing bacteria in root nodules, and for respiratory energy needed to maintain vital processes. All of these may be considered useful expenditures of photosynthate, but in a fully developed canopy there are many shaded, non productive leaves. If this excessive production of vegetation could be prevented, then higher yields of beans can expected.

Yield increase will also result from two other aspects of growth retardation:

Lower and compacter plants are better protected against lodging caused by rain and wind. (see Lit.: "Early lodging-a major barrier to higher yields" by R. L. Cooper, in: 1970 Soybean Digest, Hudson, Iowa 50643).

A reduction of the size of plants by chemicals allows a narrower planting in the field. The increased plant population will also give increased yields.

The reduction of the growth of trees and bushes saves labor in cutting hedges and trees for instance under aereal telephone or electrical lines. (In USA about 125 million dollars spent yearly for such line clearance work according to M. R. Gardner Proc Norheastern Weed Sci. Soc. 25 332-244 (1971).

The inhibition of the growth of the flora along roads, highways, canals and of the grass in lawns of athletic fields with the quaternary ammonium salts of formula I or compositions containing them saves labor for maintenance and grass-cutting.

By inhibiting the growth of new branches on fruit trees, the fruit setting and yield can be improved.

Ornamental plants can be reduced to compact pot plants by reducing hight by means of growth inhibitors.

The compounds of the invention may be sprayed on to the plant in a concentration which inhibits the growth thereof without causing any damage.

In a higher concentration the compounds of the invention are phytocidal and may be used for defoliation and dessication of the plants prior to harvesting.

The compounds of the invention may be applied in various ways for example in the form of powders, aqueous dispersions, aqueous emulsions, granules and so on.

The following test procedures are applied to demonstrate the degree of defoliation and desiccation of unlignified parts of plants above the soil occurring after application of the agents according to the invention:

1. Cotton plants having ripe capsules (60% open capsules) are sprayed with aqueous emulsions of the active substances, obtained from 25% emulsion concentrates (plot size ca. 20 m², one repeat, climate: moist-warm). The test is assessed after 14 days on the basis of the percentage fall of leaves produced by the treatment.

2. The active substances are applied either (a) as a 0.5% aqueous suspension (obtained from a 25% emulsion concentrate) or (b) as a 10% pulverulent concentrate to ca. 20 cm high cotton plants shortly before appearance of the 3rd leaf. In each case, only the surface of the leaf and the petiole of the cotyledons are treated. The plants are then allowed to stand in a greenhouse at 24° to 26° with 45 to 60% relative humidity. The test is evaluated after 3, 7 and 14 days.

In tests 1 and 2 the compound $N^1N^1$-di-isopropyl-$N^2$-methyl-$N^2$-dodecyl-formamidinium methosulfate exhibited excellent activity.

3. A field of soya-beans, variety Lee 68, was divided into plots of 30×8 feet. These were then sprayed with an aqueous dispersion of the quaternary $N^1N^1$-di-isopropyl-$N^2$-dodecyl-formamidinium iodide salt in application rates corresponding to 0.5 and 2 kg per hectare. Other plots were left untreated and served as control. At the moment of the application the soya plants had developped 9 to 10 leaves. The field was then left to grow. At the moment of harvest, 16 weeks later, the yield of these plots and the medium height of the plants in the plot were determined.

| amount applied in kg/ha | medium height of plant in inch | yield of plot in bushel/acre | (%) |
|---|---|---|---|
| 0(control) | 34 | 34,3 | (100%) |
| 0,5 | 34 | 33,7 | (98%) |
| 2 | 29 | 43,9 | (130%) |

Composition according to the invention are produced in a manner known per se by the intimate mixing and grinding of active substance of the general formula I with suitable carriers, optionally with the addition of dispersing agents or solvents which are inert to the active substances. The active substances can be obtained and used in the following forms:
 solid preparations: dusts, powder concentrates;
 water-dispersible concentrates of the active substance; wettable powders, pastes, emulsions;
 liquid preparations: solutions.

The solid preparations (dusts, and powder concentrates) are produced by the mixing of the active substances with solid carriers. Suitable carriers are, e.g. kaolin, talcum, bole, loess, chalk, limestone, ground limestone, Attaclay, dolomite, diatomaceous earth, precipitated silicic acid, alkaline-earth silicates sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

The particle size of the carriers is for dusts advantageously up to about 0.1 mm.

The concentrations of active substance in the solid preparation forms are from 0.5 to 90%.

To these mixtures may also be added additives stabilising the active substance, and/or non-ionic, anion-active, and cation-active substances, which, for example, improve the adhesiveness of the active substances on plants and on parts of plants (adhesives and agglutinants), and/or ensure a better wettability (wetting agents) and dispersibility (dispersing agents). Suitable adhesives are, for example, the following: olein/chalk mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acid, its alkali metal and alkaline-earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide, propylene oxide, polyvinyl pyrrolidones, polyvinyl alcohols, condensation products of urea and formaldehyde, as well as latex products.

Water-dispersible concentrates of active substance, i.e. wettable powders, pastes and emulsion concentrates, are agents which can be diluted with water to obtain any desired concentration. They consist of active substance, carrier, optionally additives which stabilise the active substance, surface-active substances, and anti-foam agents and, optionally, solvents. The concentration of active substance in these agents is 5 to 80%.

The wettable powders and the pastes are obtained by the mixing and grinding of the active substances with dispersing agents and pulverulent carriers, in suitable devices, until homogeneity is attained. Suitable carriers are, e.g. those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali, ammonium and alkaline-earth metal salts of ligninsulphonic acid, also alkylaryl sulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ether, the sodium salt of oleyl methyl tauride, ditertiary acetylene glycols, dialkyl dilauryl ammonium chloride, and fatty acid alkali-metal and alkaline-earth metal salts.

Suitable anti-foam agents are, for example, silicones,
 The active substances are so mixed, ground, sieved and strained with the above mentioned additives that the solid constituent in the case of wettable powders has a particle size not exceeding 0.02 to 0.04 mm, and in the case of pastes not exceeding 0.03 mm. Dispersing agents such as those mentioned in the preceding paragraphs, organic solvents and water are used in the preparation of emulsion concentrates and pastes. Suitable solvents are, e.g. the following: alcohols, benzene, xylenes, toluene, dimethylsulphoxide, N,N-dialkylated amides, N-oxides of amines, especially trialkylamines, and mineral oil fractions boiling in the range of 120° to 350°. The solvents must be practically odourless, non-phytotoxic, inert to the active substances, and not readily inflammable.

Furthermore, the compositions according to the invention can be used in the form of solutions. For this purpose the active substance (or several active substances) of the general formula I is (or are) dissolved in suitable organic solvents, mixtures of solvents, water, or mixtures of organic solvents with water. As organic solvents it is possible to use aliphatic and aromatic hydrocarbons, their chlorinated derivatives, alkylnaphthalenes, mineral oils on their own or in admixture with each other. The solutions should contain the active substances in a concentration of from 1 to 20%.

Other biocidal active substances or agents may be added to the described agents according to the invention; for the broadening of their sphere of action, it is possible to add to the new agents, for example, insecticides, fungicides, bactericides, fungistatics, bacteriostatics or nematocides. The agents according to the invention may also contain fertilisers, trace elements, etc..

Preparations of the new active substances of the general formula I are described in the following. The term 'parts' denotes parts by weight.

Wettable powder

The following substances are used for the production (a) of 25%, (b) of 10% and (c) of 50% wettable powders:

a.
25 parts of a quaternary ammonium salt of formula I
5 parts of nonylphenoxypolyethylene glycol (ethylene oxide proportion 9–10 moles),
2 parts of octylphenoxypolyethylene glycol (ethylene oxide proportion 9–10 moles),
38 parts of silicic acid,
30 parts of kaolin;

b.
10 parts of a quaternary ammonium salt of formula I
0.6 part of the sodium salt of dibutylnaphthalenesulphonic acid,
1 part of naphthalenesulphonic acid/phenolsulphonic acid/formaldehyde condensate (3:2:1),
88.4 parts of kaolin;

c.
50 parts of a quaternary ammonium salt of formula I
5 parts of sodium dibutylnaphthylsulphonate,
3 parts of naphthalenesulphonic acid/phenolsulphonic acid/formaldehyde condensate (3:2:1),
20 parts of kaolin,
22 parts of Champagne chalk.

The given active substance is drawn onto the appropriate carrier (kaolin and chalk), and the whole subsequently mixed and ground. Wettable powders are obtained having excellent wettability and suspension properties. It is possible to prepare from such wettable powders, by dilution with water, Powder concentrate The following constituents are intimately mixed and ground together to produce (a) a 10% and (b) a 25% powder concentrate:

a.
10 parts of a quaternary ammonium salt of formula I
0.6 part of sodium dibutylnaphthylsulphonate,
1 part of naphthalenesulphonic acid/phenolsulphonic acid/formaldehyde condensate 3:2:1,
10 parts of sodium aluminium silicate,
78.4 parts of kaolin;

b.
25 parts of a quaternary ammonium salt of formula I
5 parts of polyoxyethylene glycol ether of mono- or dialkyl ($C_8$-$C_9$)-phenols having 5 - 15 moles of ethylene oxide,
2 parts of octylphenoxyethylene glycol having 9–10 moles of ethylene oxide,
38 parts of silicic acid,
30 parts of kaolin.

Such powder concentrates are used to dust the foliage of cotton plants. Thus one can make suspensions of any desired concentration of active substance. These suspensions are used, for example, for the treatment of cotton plants to effect desiccation of the foliage.

Emulsion concentrate

The following constituents are mixed together for the preparation of 25% emulsion concentrates:

a.
25 parts of a quaternary ammonium salt of formula I
5 parts of a mixture of nonylphenolpolyoxyethylene and calcium dodecylbenzene-sulphate,
35 parts of 3,5,5-trimethyl-2-cyclohexen-1-one,
35 parts of dimethylformamide;

b.
25 parts of a quaternary ammonium salt of formula I
60 parts of dioctylphthalate,
15 parts of emulsifier = mixture of nonylphenolpolyoxyethylene and calcium-dodecylbenzenesulphonate.

This concentrate can be diluted with water to obtain emulsions of suitable concentrations. Such emulsions are suitable for application to the foliage of cotton plants, leguminosae, potato plants, etc..

Paste

The following substances are used for the production of a 45% paste:
45 parts of a quaternary ammonium salt of formula I
5 parts of sodium aluminium silicate,
14 parts of cetyl polyglycol ether having 8 moles of ethylene oxide,
1 part of oleyl polyglycol ether having 5 moles of ethylene oxide,
2 parts of spindle oil,
10 parts of polyethylene glycol,
23 parts of water.

The active substance is intimately mixed and ground, in suitable apparatus, with the additives. A paste is obtained from which can be prepared, by dilution with water, suspensions of any desired concentration.

The quaternary ammonium salts are produced in a manner known per se by the reaction, in an inert solvent, of a formamidine of the general formula II $$R_1 - N - CH = N - R_3 \qquad (II)$$
$$\phantom{R_1 - N - }| \phantom{CH = N - R_3}$$
$$\phantom{R_1 - N - }R_2$$

wherein $R_1$ $R_2$ and $R_3$ have the meaning given above under formula I with alkyl esters of strong acids or with an alkyl halide alkyl esters of strong acids are e.g. sulphonic acid alkyl ester or dialkyl sulphate, corresponding to formula III $$R_4 - X \qquad (III)$$

wherein $R_4$ and X have the meanings given above under formula I.

Suitable inert solvents are: dimethylformamide, dimethylsulphoxide, acetone, dioxane, ethers, or ethyl acetate, benzene, toluene, etc.

The formamidines of formula II are produced by a process in which a formamide of formula IV

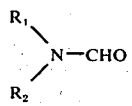

is reacted firstly with a dialkyl sulphate and subsequently with an amine of formula V

 (V)

In formulae IV and V the symbols $R_1$ to $R_3$ have the meanings given above under formula I. Formamide and dialkyl sulphate, e.g. dimethyl sulphate and diethyl sulphate, are used in the process in equimolar amounts. The compounds of formula VI

occuring as intermediates can be reacted, without being isolated, in situ with the amine of formula V.

In general, the presence of an organic aprotic solvent or diulent is advantageous for the obtainment of high yields. Thus, aliphatic halogenated hydrocarbons, such as dichloromethane, chloroform or chlorinated ethanes, and aromatic hydrocarbons as well as esters and ethereal compounds, etc., can be employed as solvents or diluents for the process.

The formamidines of formula II can be also obtained by the conversion of a formamide of formula IV with phosphorus trichlorde, phosphorus oxychloride, phosphorus pentachloride, phosgene or thionyl chloride into a chloroformamidinium chloride, and the reaction of this with an amine of formula V [cp. Weygand - Hilgetag, from p. 506 (1970)]. The reaction of an N,N-dialkylformamide of formula II with an isocyanate $R_3$—NCO, or the reduktion of a corresponding N,N,N'-trialkylurea with lithium aluminium hydride, likewise yields the formamidines of formula I [cp. British Patent Specification No. 964,640; U.S. Pat. Spec. No. 3,189,648; A Larizza et al., J. Org. Chem. 29, 627 (1964)].

The following examples serve to illustrate the described process. The temperatures are expressed in degrees Centigrade.

Example a. An amount of 129 g of $N^1,N^1$-di-isopropyl-formamide is heated with 126.3 g of dimethyl sulphate for 7 hours at 70°. The mixture is afterwards cooled; 190 g of n-dodecylamine is then added and the whole heated to 40°. An addition of 500 ml of water is subsequently made to the reaction mixture and, with cooling, the whole made alkaline with aqueous concentrated sodium hydroxide solution. The free base is extracted with chloroform. After drying and removal of the solvent by distillation, the residue is fractionated in vacuo.

The obtained $N^1,N^1$-di-isopropyl-$N^2$-n-dodecyl-formamidine is oily and has the boiling point: 110° to 113° at 0.02 Torr.

b. A solution of 213 g of dodecylformamide (1.0 mole) in 500 ml of anhydrous benzene is added dropwise at 20°–30° to a suspension of 208 g of phosphorus pentachloride (1.0 mole) in 750 ml of anhydrous benezne. After a further 12 hours of stirring at 30°, the reaction mixture is concentrated in vacuo to dryness. The residue is then dissolved in 100 ml of anhydrous benzene, and 202 g of di-isopropylamine (2.0 moles) added dropwise at 40°–50°. The whole is heated for 2 hours at 50°; water and ice are added, and the mixture rendered alkaline with aqueous sodium hydroxide solution. The organic layer is then separated and concentrated by evaporation. The $N^1,N^1$-diisopropyl-$N^2$-dodecyl-formamidine obtained as residue boils at 125°–128°C and 0.03 Torr.

c. An amount of 12.6 g (0.1 mole) of dimethyl sulphate is added to 29.6 g (0.1 mole) of $N^1,N^1$-di-isopropyl-$N^2$-n-dodecyl-formamidine dissolved in 100 ml of absolute acetone, and the whole refluxed for 3 hours. After complete removal of the acetone by distillation, there obtained $N^1,N^1$-di-isopropyl-$N^2$-n-dodecyl-$N^2$-methyl-formamidiniummethosulphate in the form of a slightly yellowish viscous oil.

Yield: 100% $n_D^{22.5°}$ = 1.4705.

d. In analogous way by reaction of $N^1N^1$-di-isopropyl-$N^2$-n-dodecyl-formamidine with methyliodide, $N^1N^1$-di-isopropyl-$N^2$-n-dodecyl-$N^2$-methyl-formamidinium-iodide is obtained in almost theoretical yield as a wax-like oil.

We claim:

1. A composition for the growth retardation of soya plants which contains as active compound an effective retarding amount of $N^1,N^1$-di-iso-propyl-$N^2$-methyl-$N^2$-dodecyl-formamidinium-methosulfate, together with a suitable inert carrier therefor.

2. A method for the retardation of the growth of soya plants which comprises applying to soya plants an effective, non-phytotoxic retarding amount of $N^1,N^2$-di-iso-propyl-$N^2$-methyl-$N^2$-dodecyl-formamidinium methosulfate.

3. A composition for the growth retardation of soya plants which contains as active compound an effective retarding amount of $N^1,N^1$-di-iso-propyl-$N^2$-methyl-$N^2$-dodecyl-formamidinium iodide, together with a suitable inert carrier therefor.

4. A method for the retardation of the growth of soya plants which comprises applying to soya plants an effective, non-phytotoxic retarding amount of $N^1,N^1$-di-iso-propyl-$N^2$-methyl-$N^2$-dodecyl-formamidinium iodide.

* * * * *